United States Patent [19]

Brookfield

[11] 3,968,876

[45] July 13, 1976

[54] SEALED CONTAINER WITH A STERILIZED HYPODERMIC NEEDLE WITHIN IT AND METHOD FOR EFFECTING THE SEALING THEREOF

[76] Inventor: Richard A. Brookfield, 25 Drumlin Road, Newton, Mass.

[22] Filed: Mar. 19, 1975

[21] Appl. No.: 559,830

[52] U.S. Cl. .............................. 206/365; 206/459
[51] Int. Cl.² .................. B65D 17/04; B65D 85/00
[58] Field of Search ............ 206/365, 459, 498, 807

[56] References Cited
UNITED STATES PATENTS

| | | | |
|---|---|---|---|
| 2,118,849 | 5/1938 | Lindsey | 206/498 X |
| 3,367,331 | 2/1968 | Brookfield | 128/221 |
| 3,759,374 | 9/1973 | Helger | 206/459 X |
| 3,783,996 | 1/1974 | Gerard et al. | 206/459 X |
| 3,809,227 | 5/1974 | Begemann | 206/459 X |

Primary Examiner—Leonard Summer

[57] ABSTRACT

A sterilized hypodermic needle is within a container having a necked receiver section and a cap section rotatably receiving the neck and providing a hermetic seal when the container is closed with the proximate ends of its sections abutting or nearly abutting and the sections have flat surfaces that are then substantially coplanar. A seal extends across the junction between the sections and is heat-sealed to flat surfaces and is of a material that will stretch, become deformed and ruptures as the container is opened.

The seal is formed by first arranging a series of containers in a side-by-side, abutting relationship. A strip of the seal-forming material is disposed across the series to overlie the junction between the sections of the several containers and is secured to the exposed flat surfaces by heat seals extending lengthwise of the strip on opposite sides of the junctions and, finally, the tape is severed transversely to free each container.

5 Claims, 6 Drawing Figures

SEALED CONTAINER WITH A STERILIZED HYPODERMIC NEEDLE WITHIN IT AND METHOD FOR EFFECTING THE SEALING THEREOF

BACKGROUND REFERENCES

U.S. Pat. No. 3,294,089
U.S. Pat. No. 3,367,331

BACKGROUND OF THE INVENTION

It is, of course, a common practice to seal containers against the accidental loss of their contents and, commonly, the seals are such that, if broken, a casual inspection will reveal the fact that the container has probably been opened with the possible loss of contents or the contamination thereof.

The prevention of contamination of container contents is of primary importance in the case of foods, beverages, and materials of various types used by doctors, dentists, and nurses that are provided in a sterile, ready-for-use condition.

Various types of seals are available and their use depends on the size and shape of a container and the material from which it is made. While heat sealing is widely used, containers of the type shown and described in the above referred-to patents have not been provided, as far as I am aware, with heat seals that can be quickly and easily broken and then provide a "telltale" that cannot be concealed and no method exists for sealing such containers on an economical production basis.

Such containers are utilized primarily for hypodermic needles of the double ended type having a hub intermediate their pointed ends, a type commonly used by the dental profession, and the containers therefor are of a type including receiver and cap sections with the receiver section having a chamber opening through a neck dimensioned to receive and frictionally retain the needle hub and the cap section having a chamber, the mouth of which is dimensioned to so frictionally receive the neck that when the cap section is seated thereon, the container is hermetically sealed but can be easily opened by rotating one section relative to the other as they are pulled apart. Such containers are of a small cross section and in practice are made from polyethylene or an equivalent plastic and are square in cross section. When properly closed, corresponding flat surfaces of the cap and receiver sections of the containers are substantially coplanar.

In the above referred-to U.S. Pat. No. 3,294,089 reference is made to the fact that needles packaged within such containers can be sterilized by any suitable process and may be heat sealed along the line of abutment between the two portions of the closed containers. The difficulty with heat sealing such containers in the above manner is that a heat seal that permits the container to be opened with the required ease leaves no evidence that it has been broken while a heat seal of a strength that would rupture the container material can be ruptured manually, if at all, only with great difficulty.

THE PRESENT INVENTION

The general objective of the present invention is to provide both a sealed container for a sterilized hypodermic needle, and a method of sealing them, the container of the type having receiver and cap sections including mating, rotatable, frictionally engaged portions providing a hermetic seal when the container is closed and the seal, when broken, providing a tell-tale that cannot be concealed.

In the case of the sealed containers, the general objective is attained by providing them with flat surfaces that are substantially coplanar when the container is closed and a seal that extends across the junction between the container sections and is secured by heat seals to each of them, the seal of a material that will stretch somewhat and be permanently deformed when it ruptures. It is preferred that the container sections be of a cross sectional shape providing at least two parallel flat surfaces, and desirably square.

In the case of the method, the desired objectives are attained by assembling a series of such containers in an abutting, side-by-side relationship with flat surfaces exposed, extending a length of a tape of the seal-forming material across the containers of the series and in a position covering the junction between the two sections of each container, heat sealing the tape to each section of each container and then severing the tape to free each sealed container from the others.

BRIEF DESCRIPTION OF THE DRAWINGS

In the accompanying drawings, there is shown an illustrative embodiment of a container with a sterilized hypodermic syringe within it and the method of sealing the same

THE PREFERRED EMBODIMENT OF THE INVENTION

Figure 1:
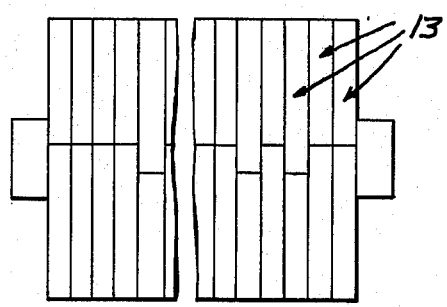
FIG. 1 is a somewhat schematic view of a series of containers assembled to be sealed, each with a sterilized hypodermic needle within it.

The preferred embodiment utilizes hypodermic needles and containers therefor in accordance with the disclosures of U.S. Pat. Nos. 3,294,089 and No. 3,367,331.

The hypodermic needle is generally indicated at 10 and has a cannula 11 having at its ends oppositely beveled points and a plastic hub 12 molded thereon between said ends, the hub 12 of substantial length and square in cross section. The hub 12 in practice, is nylon.

A container for the needle 10 is generally indicated at 13 and includes a receiver section 14 and a cap section 15, both sections square in cross section and molded, preferably from polyethylene. In practice, the width of each flat surface is three-sixteenths inch and the over-all length of the container is two and one-half inches. The receiver section 14 has a chamber 16 opening through a slightly tapered neck 17 of circular cross section and is dimensioned to freely receive one end of the needle 10 and to frictionally hold its hub 12 with a substantial portion exposed. The cap section 15 has a chamber 18 dimensioned freely to receive the remainder of the needle 10 with its mouth rotatably receiving the neck within it and dimensioned relative to the neck to provide a hermetic container seal when the cap section is securely seated thereon. When the container is closed the proximate ends of its sections may abut. Hermetic sealing does not require such abutment but only that the cap section be securely seated on the neck of the receiver section and in production there is often a slight space between their proximate ends. While the friction fit of the neck 17 within the mouth of the chamber 18 provides a tight seal, the container sections may be readily turned relative to each other as the two sections are being pulled apart to open the container 13 or pushed together to close it.

As the needle 10 is sterilized within the container 13, it is important to ensure that the container has not been opened and again closed before use of the needle 10. To that end, a seal 19 is employed, the seal 19 in the form of a strip overlying the junction between the receiver and cap sections and secured to corresponding flat surfaces of said section by transverse heat seals, the heat sealed areas being indicated at 20, each spaced from the junction and preferably of a color contrasting with that of the container section. In practice, the seals 19 are formed from a strip of material five-eighths of an inch in width and the heat seals 20 are each about an eighth of an inch in width leaving an intermediate portion that is free. The material from which the seals 19 are formed is one that will readily rupture as the container 13 is opened and will stretch somewhat before rupturing and become permanently deformed. For this purpose, polyethylene, the thickness of which is in the order of one or two thousanths of an inch, has proved satisfactory. While in the ideal assembly of a container corresponding flat surfaces of its receiver and cap sections are co-planar, in production this result is not precisely attained but such corresponding surfaces are so nearly co-planar that the sealing strip may be securely heat sealed to both sections without difficulty.

Figures 4, 5, 6:
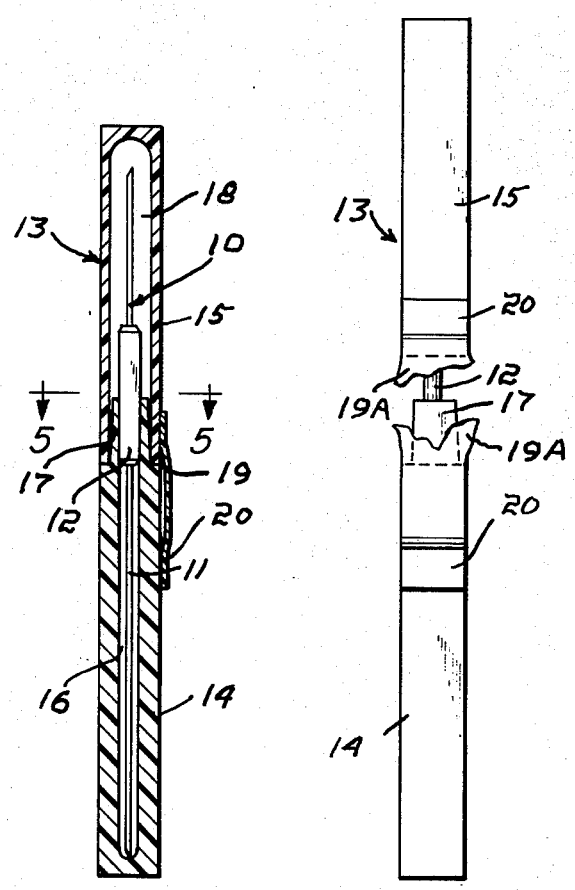
FIG. 4 is a section, on an increase in scale, taken lengthwise of a container through its seal.
FIG. 5 is a section taken approximately along the indicated line 5—5 of FIG. 4, illustrating the stretching and rupturing of the seal as one container section is turned relative to the other as they are pulled apart to open the container.
FIG. 6 is a view showing the ruptured seal with the deformed tell-tales or "flags" on each container section.

As above stated, the containers 13 are manually opened, usually by a combined turning and pulling action. It will be noted from FIG. 5 that such turning of one container section relative to the other causes a corner to stretch the seal radially outwardly as well as transversely with the seal rupturing to provide tell-tales or flags 19A on each container section that prevent the ruptured edges from matching thus making it impossible to conceal the fact that the container 13 has been opened.

Figure 2:
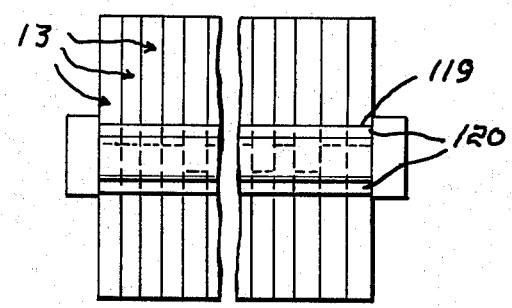
FIG. 2 is a like view illustrating the heat sealing of a length of seal-forming material to the receiver and the cap sections of the several containers.
Figure 3:
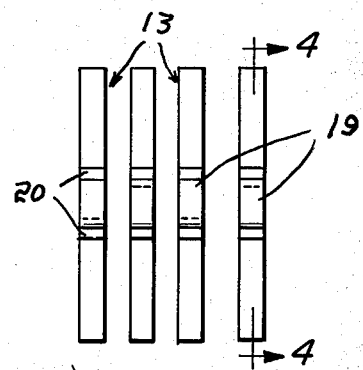
FIG. 3 is a view on the scale of FIGS. 1 and 2, showing a plurality of containers freed by severing the heat-sealed length.

The containers 13 are sealed by assembling a series of them on a flat support in a side-by-side, abutting relationship. A strip 119 of the seal-forming material is then extended across the series of containers in a position covering the junctions between their sections and then continuous heat seals are completed across both sections of each of the containers 13 of the assembled series but spaced from the junctions, see FIG. 2, the heat sealed areas being indicated at 120. The strip 119 is then severed to free the sealed containers, see FIG. 3. It will be noted that the cap and receiver sections of the containers 13 are not of the same length and it is preferred that all the containers of the series being heat sealed be so positioned that the junctions between their sections are transversely aligned. The width of the strip 119, however, is not only adequate to permit proper heat sealing if the proximate ends of the container sections do not abut but also in the event that, see FIG. 1, the position of one or more of the containers 13 of the series is reversed relative to the others.

From the foregoing, it will be apparent that the seals 19, while not interfering with the ease with which the containers 13 may be opened, provide positive tell-tales or flags 19A once they are opened and such seals are well adapted to meet production requirements on an economical basis.

I claim:

1. A sealed container with a sterilized hypodermic needle within it, said container comprising a receiver section provided with a cylindrical neck at one end and having a chamber opening through the neck and a cap section having a chamber receiving the neck within it, the mouth of the cap portion and the neck being of a fit permitting the sections to be turned relative to each other but dimensioned to establish a friction fit such as to provide a hermetic seal, said container portions including external, flat-surfaced portions that are substantially co-planar, and a seal in the form of a strip overlying said flat-surfaced portions and extending across the junction between the container sections, the container and the sealing strip being of heat sealable material, and heat seals, one between each flat-surfaced portions and said strip, said sealing strip also being of a material that will stretch somewhat and be deformed before rupturing, the seal stretching and rupturing as one container section is turned relative to the other as the sections are pulled apart with the proximate ends of the ruptured seal permanently deformed.

2. The package of claim 1 in which the heat seals are so spaced from the junction between the container sections that any unsealed seal section overlies the proximate ends of the container sections whereby the ruptured stretched ends of the seal are free as signals that the sterility of the needle may have been lost.

3. The package of claim 1 in which the seal is of a color contrasting with that of the container sections.

4. The package of claim 1 in which the container sections are square in cross section.

5. The package of claim 1 in which the seal is polyethylene.

* * * * *